United States Patent [19]

Ludwig et al.

[11] 4,293,539

[45] Oct. 6, 1981

[54] CONTROLLED RELEASE FORMULATIONS AND METHOD OF TREATMENT

[75] Inventors: Nelson H. Ludwig; Earl E. Ose, both of Greenfield, Ind.

[73] Assignee: Eli Lilly and Company, Indianapolis, Ind.

[21] Appl. No.: 74,684

[22] Filed: Sep. 12, 1979

[51] Int. Cl.³ .............................................. A61K 9/22
[52] U.S. Cl. ...................................... 424/19; 424/22; 128/260
[58] Field of Search ................... 128/260; 424/14–22

[56] References Cited

U.S. PATENT DOCUMENTS

| | | | |
|---|---|---|---|
| 3,056,724 | 10/1962 | Marston | 424/22 |
| 3,507,952 | 4/1970 | Rednick et al. | 424/22 |
| 3,535,419 | 10/1970 | Siegrist | 424/22 |
| 3,736,646 | 6/1973 | Schmitt et al. | 29/458 |
| 3,773,919 | 11/1973 | Boswell et al. | 424/22 |
| 3,844,285 | 10/1974 | Laby | 128/260 |
| 3,887,699 | 6/1975 | Yolles | 424/19 |
| 3,972,999 | 8/1976 | Tsuk | 424/78 |
| 3,976,071 | 8/1976 | Sadek | 128/260 |
| 3,991,766 | 11/1976 | Schmitt et al. | 128/335.5 |
| 4,011,312 | 3/1977 | Reuter | 424/78 |
| 4,076,798 | 2/1978 | Casey et al. | 424/22 |
| 4,118,470 | 10/1978 | Casey et al. | 424/19 |
| 4,166,107 | 8/1979 | Miller et al. | 424/19 |
| 4,166,800 | 9/1979 | Fong | 252/316 |

*Primary Examiner*—Shep K. Rose
*Attorney, Agent, or Firm*—Charles W. Ashbrook; Arthur R. Whale

[57] ABSTRACT

Controlled release formulations useful in the prolonged treatment and control of microbial infections in animals are comprised of a microbial agent intimately dispersed throughout a copolymer derived from lactic acid and glycolic acid. A method for providing protection to animals for extended periods of time following a single administration is provided.

48 Claims, No Drawings

CONTROLLED RELEASE FORMULATIONS AND METHOD OF TREATMENT

BACKGROUND OF THE INVENTION

This invention concerns formulations capable of supplying an effective dose of a drug to an animal over a prolonged period of time, and a method of preventing and treating diseases.

The concept of administering a drug to an animal in a form which is capable of supplying an effective dose of the drug to the animal over a prolonged period of time is known in the art. Yolles, for example, in U.S. Pat. No. 3,887,699, describes a formulation comprised of drug intimately dispersed throughout a biodegradable polymeric material which is in the form of a solid film which is implanted subcutaneously into the animal. Schmitt et al., in U.S. Pat. Nos. 3,736,646 and 3,875,937, describe polymers and copolymers which are useful as surgical devices and delivery systems. Boswell et al., in U.S. Pat. No. 3,773,919, disclose formulations which include a lactide polymer and which allegedly permit prolonged release of drugs for a controlled period of time.

The use of polymeric formulations for the slow release of drugs in the treatment of various diseases in animals has suffered in a number of respects. The polymers currently available generally are prepared in such a way that removal of the polymerization catalyst from the polymer is impossible or impracticable. As a result, when the polymer is placed in an animal and degrades over a period of time, undesirable quantities of polymerization catalysts such as metal oxides or strong acids remain in the animal tissues. This is particularly undesirable when the animals so treated are used for meat or other food production. Additionally, most of the polymers known in the art have physical characteristics which necessitate their administration by implantation; see Yolles, U.S. Pat. No. 3,887,699. Such implantation requires the services of one skilled in surgical methods. Moreover, as pointed out by Siegrist et al., in U.S. Pat. No. 3,535,419, the slow release polymeric formulations currently available lack a sufficiently controlled rate of release to be predictable over a useful period of time. This aspect is particularly critical when the active agent being administered can become lethal at elevated doses, and ineffective at insufficient doses.

An object of this invention is to provide formulations comprising a pharmacological agent which is effective prophylactically or therapeutically in combination with a copolymer capable of uniformly releasing the active agent in effective amounts over a predetermined period of time. A further object is to provide copolymeric formulations capable of complete biodegradation into readily metabolized substances. Another object is to provide formulations which can be administered by injection and which, when biodegraded, leave no undesirable residues in animal tissues. Still another object of the invention is to provide a method for effectively preventing the formation of infectious diseases in animals and treating animals suffering from infectious diseases.

SUMMARY OF THE INVENTION

The present invention provides novel formulations which permit the controlled delivery of pharmaceuticals to animal systems, and a method of prophylactic and therapeutic treatment of infectious diseases. More particularly, the invention provides a controlled release formulation, capable of delivering an effective dose of active ingredient over a prolonged period of time and biodegradable into readily metabolized substances, comprising an effective amount of active ingredient and pharmaceutically acceptable diluents and carriers therefor, intimately dispersed throughout a copolymer derived from about 60 to about 95 weight percent lactic acid and about 40 to about 5 weight percent glycolic acid, said copolymer having an inherent viscosity in chloroform of about 0.08 to about 0.30, a molecular weight of about 6000 to about 35000, and said copolymer being substantially free of polymerization catalyst.

A preferred formulation according to this invention comprises a prophylactically or therapeutically effective amount of a pharmaceutical agent intimately dispersed throughout a copolymer derived from about 60 to about 90 percent lactic acid and about 40 to about 10 percent glycolic acid having a viscosity in chloroform of about 0.10 to about 0.25 and a molecular weight of about 15,000 to about 30,000.

A more preferred formulation is one wherein the copolymer contains from about 70 to about 80 percent lactic units and about 30 to about 20 percent glycolic units having an inherent viscosity of about 0.13 to about 0.23.

Pharmaceutical agents utilized in the formulations of this invention include antimicrobial agents, vitamins, anti-inflammatory agents, hormones, anti-bloat agents and the like. Particularly preferred pharmaceutical agents used in the formulations include antimicrobial agents such as the tetracyclines, penicillins, cephalosporins, macrolide antibiotics, sulfa drugs, aminoglycosides and other agents specifically useful in the treatment and prevention of microbial infections.

This invention additionally provides a method for treating animals suffering from a microbial disease or suspected of developing a microbial infection comprising administering to the animal a copolymeric formulation capable of releasing an effective amount of active drug over a prolonged period of time. The method is preferably carried out by subcutaneously or intramuscularly administering a copolymer derived from about 60 to about 95 weight percent lactic acid and about 40 to about 5 weight percent glycolic acid having an inherent viscosity in chloroform of about 0.08 to about 0.30, said copolymer having uniformly dispersed therethrough an antimicrobial amount of an active agent and other suitable diluents and excipients, said formulation being uniformly dispersed through a suitable carrier or diluent to facilitate parenteral administration.

A preferred method of treatment according to this invention comprises subcutaneously administering to an animal suffering from or susceptible to microbial infection and in need of treatment an effective amount of a controlled release copolymeric formulation containing a compatible antimicrobial agent.

DETAILED DESCRIPTION OF THE INVENTION

A copolymeric material ideally suited to the controlled release of an effective amount of a pharmaceutical agent to an animal such that the animal can be effectively treated with a minimum of administrations has been discovered. Such copolymeric material is prepared by a process which permits the substantially complete removal of polymerization catalyst, thereby permitting the total degradation of the copolymeric matrix in a biological system without the concomitant accumulation of toxic residues in animal tissues. This aspect of the invention is of particular significance in the treatment of animals utilized in the production of meat for human consumption.

The copolymers required for the formulations of this invention are prepared by condensation of lactic acid and glycolic acid in the presence of a readily removable polymerization catalyst. Such catalysts include strong acid ion-exchange resins in the form of beads or similarly hard structures which are easily removed by filtration or similar techniques. Particularly preferred polymerization catalysts include commercially available strong acid ion-exchange resins such as amberlite IR-118(H), Dowex HCR-W (formerly Dowex 50W), Duolite C-20, Amberlyst 15, Dowex MSC-1, Duolite C-25D, Duolite ES-26 and related strong acid ion-exchange resins. The catalyst is added to a mixture of about 60 to about 95 parts by weight of lactic acid and about 40 to about 5 parts by weight of glycolic acid. The amount of catalyst utilized is not critical to the polymerization, but typically is from about 0.01 to about 20.0 parts by weight relative to the total weight of combined lactic acid and glycolic acid. The polymerization generally is carried out in the absence of solvents; however, organic solvents such as dimethylsulfoxide or N,N-dimethylformamide can be utilized if desired. The polymerization reaction routinely is carried out in a reaction system equipped with a condensing system, thereby permitting the collection and removal of water that is formed, as well as facilitating the removal of any lactide and glycolide byproducts that are formed. The polymerization reaction generally is conducted at an elevated temperature of about 100° to about 250° C., and at such temperature is usually substantially complete within about 48 to about 96 hours. Ideally, the reaction can be carried out under a reduced pressure, thereby further facilitating removal of water and byproducts.

The copolymer thus formed is readily recovered by simply filtering the molten reaction mixture to remove substantially all of the strong acid ion-exchange polymerization catalyst. Alternatively, the reaction mixture can be cooled to room temperature and then dissolved in a suitable organic solvent such as dichloromethane or acetone and then filtered by normal means so as to remove the solvent-insoluble strong acid ion-exchange resin. The copolymer then is isolated by removal of the solvent from the filtrate, for instance by evaporation under reduced pressure. Further purification of the copolymer can be accomplished if desired by re-dissolving it in a suitable organic solvent and further filtration, including the use of standard filter aids if desired.

The copolymer thus formed is required in the formulations and method of treatment provided by this invention. Such copolymers, while not amenable to exact structure elucidation, are characterized as having a molecular weight of about 6000 to about 35000, and preferably from about 15000 to about 30000. The copolymers are unique in that they are classified as high molecular weight substances having an inherent viscosity from about 0.08 to about 0.30 when measured by standard techniques utilizing an Ubbelohde viscometer in which chloroform has an efflux time of about 51 seconds at 25° C. The inherent viscosity of the copolymers is determined by the following equations $$\eta r = t/t_o \quad \eta \text{inh} = (\ln \eta r / C)$$

wherein:
$\eta r$ is relative viscosity;
$t_o$ is efflux time of solvent;
$t$ is efflux time of the solution;
$\eta \text{inh}$ is inherent viscosity;
C is concentration in grams per 100 ml. of solvent; and
ln is logarithm.

The copolymers utilized in the formulations of this invention are additionally unique in that they are capable of providing a controlled release of pharmaceutical agents heretofore unavailable, in addition to being of such physical makeup which permits their suspension in a suitable vehicle, thus allowing convenient administration, for example via subcutaneous injection. The formulations alternatively can be administered orally or by implantation.

The formulations comprehended by this invention comprise an effective amount of a pharmacological agent uniformly admixed and dispersed throughout the copolymeric matrix hereinabove described. The formulations contain from about 5 to about 85 percent by weight of active ingredient, ideally about 20 to about 75 percent, and more preferably about 30 to about 60 percent. The pharmacologically active agents which can be utilized in the formulations include those agents commonly employed in the treatment of the particular disease sought to be prevented or treated with the formulation of the invention. Commonly used active agents include antibiotics such as the tetracyclines, particularly chlortetracycline, oxytetracycline, doxycycline and tetracycline; penicillins such as ampicillin, benzylpenicillin, penicillin V; cephalosporanic acids such as the cephalosporin oximes; cephalosporin salts; oxycephalosporins, the cloxacillins and the like. Additional antibiotics routinely used in the formulations of the invention include streptomycin, novabiocin, neomycin, sulfonamides, erythromycin, colistin, lincomycin, nalidixic acid, apramycin, salinomycin, nigericin, kanamycin, kitsamycin, tylosin, furaltadone, vancomycin, thiostrepton, gentamycin, tobramycin, spiramycin, ristocetin, soimycin and the like. Preferred formulations contain as active ingredient an antimicrobial agent selected from erythromycin, spiramycin, tylosin, the tetracyclines, oxytetracycline, doxycycline, neomycin, lincomycin and cephalosporins, particularly cephalosporin oximes. A particularly preferred formulation of the invention in one comprised of the copolymeric matrix and about 30 to about 60 percent by weight of the macrolide anti-biotic tylosin, in addition to commonly used pharmaceutical diluents, excipients and carriers.

The formulations provided by this invention can be prepared in any of a number of ways. A preferred method of preparation comprises dissolving a suitable amount of the aforementioned copolymer in an organic solvent that is readily removed by evaporation, and then adding the desired amount of pharmacologically active agent. For example, about 50 grams of a copolymer derived from about 80 weight percent of lactic acid and about 20 weight percent of glycolic acid, said copolymer having an inherent viscosity of about 0.23, can be dissolved in about 200 to about 400 ml. of a suitable organic solvent such as dichloromethane, acetone, diethyl ether, tetrahydrofuran, chloroform, or the like. A pharmacological agent such as tylosin, in the amount of about 30 grams, can be added to the dissolved copolymer. The solution thus formed can be spray dried by conventional methods so as to obtain a formulated solid product having uniform mixing of copolymer and active agent and being of substantially uniform particle size. Such formulation can be utilized in the treatment of microbial diseases in animals. For instance, the formulation can be utilized in the treatment of pneumonia in young calves. If desired, a suitable amount of the formulation can be suspended in a suitable vehicle such as sesame oil and injected subcutaneously. Such treatment provides the slow release of active ingredient to the animal, such that the effective dose of active drug is from about 4 to about 10 mg. per pound per day for a period of about 6 to 10 days.

The formulations of the invention can alternatively be prepared by dissolving the copolymer and active agent in a suitable organic solvent, followed by removal of the solvent by evaporation. The copolymeractive agent formulation next can be melted and the melt can be extruded into rods having a diameter of about 2.0 to about 7.0 millimeters in diameter. The extruded rods can be cut to desired lengths so as to provide a specific amount of active agent. For example, a formulation which includes about 50 grams of the antibiotic tylosin and about 100 grams of a copolymer derived from about 70 to about 80 weight percent of lactic acid and about 30 to about 20 percent glycolic acid, said copolymer having an inherent viscosity of about 0.13 to about 0.23, can be melt extruded into rods having a diameter of about 5.0 millimeters. Such rods of formulated tylosin are, when cooled to room temperature, quite hard and are translucent, and accordingly give the appearance of an amber colored glass. Such glass can be cut into desired lengths so as to obtain the desired dose of tylosin antibiotic. The glass rod of about 40 to 80 mm. can be implanted under the skin of the animal to be treated, or alternatively the glass can be ground into small particles and passed through an appropriate wire sieve, for example from about 60 to about 160 mesh, so as to obtain formulated copolymer-tylosin that is easily suspended in an oil such as sesame oil or the like. The oil can then be injected subcutaneously to an animal such as a calf to provide therapeutic or prophylactic treatment against microbial infection such as pneumonia.

The formulations provided by this invention can contain, in addition to the copolymer matrix and the active ingredient, other substances commonly utilized in medicinal formulations. Diluents, carriers, binders, excipients and adjuvants routinely incorporated in such formulations include gum tragancanthe, acacia, corn starch, gelatin, alginic acid, magnesium stearate, aluminum monostearate, beeswax, sucrose, lactose, methylparaben, propylparaben, mannitol, propylene glycol, microcrystalline cellulose, calcium silicate, silica, polyvinylpyrrolidone, cetostearyl alcohol, cocoa butter, polyoxyethylene sorbitan monolaurate, ethyl lactate, sorbitan trioleate, calcium stearate, talc and the like. Carriers commonly utilized in administering the formulations by injection include mineral oil, peanut oil, sesame oil, as well as aqueous solutions such as normal sodium chloride solution or sodium carboxymethyl cellulose in water, as well as aqueous polyvinylpyrrolidone.

The formulations contemplated herein can, if desired, include more than one pharmacologically active ingredient. Certain antibacterial agents, for example, have an immediate onset of action, while others may not be completely effective until normal treatment has been carried out repeatedly. According to this invention, a fast acting pharmacological agent can be combined with the aforementioned copolymer matrix, together with a slower acting active agent. Administration of such formulation is then effective to treat and protect the host animal against a particular disease for several days, weeks, or even months.

An additional aspect of this invention is a method of treatment utilizing the novel formulations hereinabove described. The method of treatment provided herein comprises administering to an animal suffering from an infectious microbial disease and in need of treatment, or to an animal suspected of developing a disease and in need of prophylactic treatment, a suitable amount of copolymer derived from about 60 to about 95 weight percent of lactic acid and about 40 to about 5 weight percent of glycolic acid, said copolymer having an inherent viscosity in chloroform of about 0.08 to about 0.30, and said copolymer having admixed uniformly therethrough an effective amount of therapeutic agent, said amount of administered copolymertherapeutic agent being such that the animal receives an effective amount of therapeutic agent over a prolonged and predetermined period of time.

A number of animals, particularly food producing animals such as swine, ruminants, poultry and the like, are inflicted with a variety of diseases at birth and during early stages of development. Many such diseases are transmitted through the parent directly to the offspring. One such disease commonly suffered by young pigs is mycoplasmal pneumonia. Similarly, numerous young calves suffer and die each year from pneumonia contacted as a result of exposure to severe weather conditions.

There is substantial economic loss suffered each year due to deaths caused by these various diseases. While therapeutic agents are known which are effective against such diseases, no practical and effective means has been heretofore developed for the administration of such agents to young animals. For example, the owner of a herd of several hundred young calves simply is unable to treat such herd with a therapeutic agent which requires multiple daily administrations. While some therapeutic agents are orally effective and can be added to feed or to water, very young animals such as newborn pigs and calves simply do not consume sufficient quantities of these substances to obtain a dose of active agent sufficiently large to effectively treat the disease. Moreover, substantial losses can be obviated if newborn animals could be protected from diseases by prophylactic treatment until such time that the animals have a sufficiently developed autoimmune system to effectively combat diseases to which they are exposed.

According to the method of this invention, a controlled release formulation as described hereinabove is administered to an animal so that the animal receives, with a single administration, an effective dose of therapeutic agent continuously for a period of several days. For example, a controlled release formulation comprised of about 2.0 to about 12.0 grams of an antibiotic such as tylosin or oxytetracycline and about 1.0 to about 12.0 grams of a copolymer derived from about 80 weight percent of lactic acid and about 20 weight percent glycolic acid can be extruded into a glass rod, ground, screened to uniformity through an 80–140 mesh screen, and suspended in sesame oil containing about 1 to about 2 percent of aluminum monostearate and about 1 to about 2 percent of beeswax, for convenient subcutaneous administration to a young calf weighing about 100 to about 200 pounds. Such treatment is effective for releasing to the animal the active ingredient at the rate of about 1.0 to about 15.0 mg. per pound each day for about eight days. Such treatment is particularly effective for the therapeutic and prophylactic therapy of pneumonia in calves.

While the controlled release formulations are preferably administered by subcutaneous or intramuscular injection according to this invention, treatment via alternative routes is also contemplated. For example, the active agent can be formulated with the copolymer matrix and additional binders and carriers and molded into a suitable bolus for convenient oral administration. Alternatively, the controlled release formulations can be extruded into rods or the like and implanted under the animals skin according to standard techniques. Additionally, the formulations can be enclosed or encapsulated in a device suitable for administration as a suppository or as an intrauterine or intramammary device. Such formulations are thus effective for prolonged treatment of mastitis and similar diseases.

The particular amount of controlled release formulation required for a particular treatment will vary, depending upon the species, age and weight of the host animal being treated, the particular disease to be guarded against, or treated, as well as the specific therapeutic agent selected for the treatment, the route of administration and the frequency. Generally, an amount of formulated controlled release drug will be administered so that the daily payout of active ingredient is comparable to or somewhat less than the recommended daily dosage of that particular active drug. For example, tylosin is known to be effective in the treatment of contagious calf pneumonia, diphtheria, foot rot, metritis and pneumonia in cattle, and erysipelas, pneumonia, dysentery and arthritis due to mycoplasma in swine. The effective dose of tylosin in the treatment of such diseases is from about 1.0 to about 20.0 mg. per pound of animal body weight, when administered intramuscularly. According to the method of this invention, a controlled release formulation of copolymer and tylosin is administered so that the daily dose of tylosin is from about 0.5 to about 15 mg. per pound of animal body weight. The formulation is such that total payout of the active ingredient is accomplished within about 5 to about 10 days, generally in about 7 or 8 days. It is contemplated that in one aspect of this invention, young calves (from 2 to about 25 days old) can be effectively protected from and treated for a disease such as pneumonia by the subcutaneous administration of a formulation of this invention containing about 2.0 to about 10.0 grams of tylosin once every 7 to 10 days, the total number of such treatments being from 1 to about 4, or as needed by the severity of the condition being treated or guarded against.

The formulations and method of treatment provided by this invention have been evaluated in several tests designed to show their utility and efficacy. One such test consisted of treating calves injected with varying dosages of tylosin in controlled release formulations. Tylosin was formulated with a copolymer derived from about 80 weight percent lactic acid and about 20 weight percent glycolic acid, having a viscosity of about 0.20. The formulations were extruded into glass rods. The glass rods were ground, passed through a 60 onto a 140 mesh screen (about 100 to 200 micron particle size) and then suspended in 5 ml. of sesame oil. Three formulations were prepared such that the effective doses of tylosin were 2.5 mg./lb./day, 5.0 mg./lb./day and 7.5 mg./lb./day respectively. The formulations also contained about 1 to 2 percent by weight of beeswax and about 1.5 to about 2.5 percent by weight of aluminum monostearate, which ingredients aided syringability. The formulations thus prepared were administered subcutaneously in the neck of young calves suffering from naturally occuring bacterial pneumonia. Fifteen calves were held as controls and received no medication. Three groups of fifteen calves each were treated on day zero and again on day 7 with the three respective formulations. Mortality was determined after fourteen days. The results of the test are presented in Table I.

TABLE I

| Dose of Tylosin from controlled release formulations mg./lb./day | Mortality deaths out of fifteen |
| --- | --- |
| Control | 10 |
| 2.5 | 4 |
| 5.0 | 6 |
| 7.5 | 3 |

In a similar study, twenty young calves suffering from naturally occuring pneumonia were treated subcutaneously on day zero and again on day seven with a tylosin formulation designed to release about 4.0 mg. per pound per day for about seven days. Ten infected calves were held as controls and not treated. During the course of the experiment, clinical observations were made, including nasal discharge, ocular discharge and diarrhea. Rectal temperatures and mortality were recorded. Of the control group receiving no medication, six of the ten infected animals died by the twenty-first day (60 percent mortality). Of the treated group, only five of the twenty infected animals had died (25 percent mortality). Table II below lists the average daily rectal temperatures of the control group and the treated group. The data demonstrates that the treated group had uniformly lower temperatures than the control group, thus indicating that the treated group suffered a less severe infection than the control group.

TABLE II

| Average Daily Rectal Temperatures in Excess of 100° F. | | | | | | | | | |
| --- | --- | --- | --- | --- | --- | --- | --- | --- | --- |
| | Days of Experiment | | | | | | | | |
| | 1 | 2 | 5 | 7 | 8 | 9 | 12 | 13 | 14 |
| Control Group | 2.4 | 3.2 | 2.5 | 2.8 | 3.9 | 3.5 | 3.0 | 3.2 | 3.4 |
| Treated Group | 2.5 | 2.5 | 2.1 | 2.3 | 3.3 | 2.7 | 2.0 | 2.4 | 2.1 |

A particularly preferred prophylactic treatment according to this invention comprises the administration to young pigs an effective amount of a formulation of this invention for the prevention of mycoplasmal pneumonia caused by *Mycoplasma hypopneumoniae*. This particular disease has been estimated to occur in over half of the pigs in the world and to cause an average economic loss of about one dollar per head. This particular disease is transmitted from the sow to one or more newborn pigs in a litter within a few days after birth of the litter. Because of its contagious nature, the disease can be rapidly transmitted to most of the other newborn pigs in the litter. While no drug is known which is effective against this disease after the animal has been infected, certain drugs, including tylosin and chlortetracycline, are effective prophylactically when administered to the animal prior to contact with the disease. While daily injections of such active agents would probably control the disease, such treatment is impracticable due to the labor required, the cost, the injection site irritation and related factors. Moreover, feed additives and the addition of the therapeutic agent to a watering trough is ineffective simply because the newborn animals do not consume sufficient quantities of these substances in order to injest an effective dose of the therapeutic agent.

The method of the present invention affords a means whereby newborn and young animals can be effectively protected against infection by mycoplasmal pneumonia. Such method accordingly contemplates treatment of young animals with an antimycoplasmal agent-copolymer formulation such as those hereinabove described. Such formulation can be administered at birth and periodically thereafter as required up to weaning, thus providing effective prophylactic treatment against the disease. Typical formulations utilized for the treatment of mycoplasmal pneumonia in young animals according to the method of this invention are comprised of the aforementioned copolymer, derived from about 60 to about 95 percent lactic acid and about 40 to about 5 percent glycolic acid, and a suitable antimycoplasmal agent such as tylosin and chlorotetracycline. A particularly preferred method of prophylactic treatment according to the invention comprises administering a controlled release formulation of the aforementioned copolymer and the antibiotic tylosin. While tylosin is reported to be ineffective as a treatment for mycoplasmal pneumonia, it is surprisingly and significantly effective prophylactically against such disease when administered according to the method of this invention. For instance, formulations comprised of about 100 to about 1500 mg. of tylosin intimately dispersed throughout from about 100 to about 1500 mg. of a copolymer derived from about 70 to about 80 percent lactic acid and about 30 to about 20 percent glycolic acid, having a viscosity of about 0.13 to about 0.23, can be administered to a newborn pig at the rate of about 10 to about 50 mg/kg about once every 7 to 14 days. Such treatment is effective in uniformly and continuously protecting the young animal from contacting mycoplasmal pneumonia.

As previously pointed out, the formulations can be administered by any of several ways. For the treatment of young pigs, the formulations ideally are extruded into rods, and the rods are cut into appropriate length, for example about 20 mm., to give the desired dosage of active ingredient. Such rod can be implanted subcutaneously in the animal. Alternatively, the formulated rods can be ground to uniformity and suspended in a suitable carrier for convenient subcutaneous or intramuscular injection.

The following detailed examples are presented by way of illustration of certain specific embodiments of the invention.

EXAMPLE 1

Preparation of Copolymer Matrix

To a 3-neck round bottom flask equipped with a condenser and thermometer were added 355.0 g. of lactic acid, 145.0 g. of glycolic acid and 5.0 g. of Dowex HCR-W2-H ion exchange resin. The mixture was stirred and heated to 130° C. for three hours, during which time 200 ml. of water were distilled and collected. After discarding the water thus produced, stirring and heating were continued and the pressure was gradually reduced by vacuum over three hours, after which time the temperature of the reaction mixture had increased to 150° C. at a final pressure of 5 torr. An additional 5.0 g. of Dowex HCR-W2-H catalyst was added to the reaction mixture, and the mixture then was heated to 170° C. at 5.0 torr for twenty-four hours, and then at 185° C. at 5.0 torr for an additional 48 hours. The molten reaction mixture was filtered to remove most of the ion exchange polymerization catalyst, and the filtrate was allowed to cool to room temperature to give 300 g. of a copolymer having about 65 percent lactic units and 35 percent glycolic units. The copolymer was analyzed by proton nuclear magnetic resonance spectrometry and shown to consist of about 65 percent lactic units.

The viscosity of the copolymer was determined in a Ubbelohde viscometer in which chloroform had an efflux time of 51 seconds at 25° C. The copolymer was dissolved in chloroform at a concentration 0.50 g. per 100 ml. of solvent. Inherent viscosity of the copolymer was then determined according to the formulas:

$$\eta r = (t/t_o) \quad \eta inh = (\ln \eta r / C)$$

wherein:
$\eta r$ = relative viscosity
$t_o$ = efflux time of solvent (CHCl$_3$)
$t$ = efflux time of solution
$\eta inh$ = inherent viscosity
C = conc. in grams/100 ml.

The inherent viscosity of the copolymer was determined to be 0.19 dl/g.

EXAMPLE 2

Following the general procedure set forth in Example 1, 710 g. of lactic acid and 290 g. of glycolic acid were condensed in the presence of a total of 40.0 g. of Amberlyst 15 ion exchange polymerization catalyst to afford 600 g. of copolymer derived from about 70 percent by weight lactic acid and about 30 percent by weight glycolic acid. The copolymer had the following viscosity: 0.18 dl/g.

EXAMPLE 3

Following the general procedure of Example 1, 355.0 g. of lactic acid were condensed with 145.0 g. of glycolic acid in the presence of a total of 10.0 g. of Amberlyst 15 ion exchange polymerization catalyst. After removing the catalyst by filtration, there was provided 300 g. of copolymer comprised of about 70 percent of lactic units and 30 percent of glycolic units. The copolymer exhibited the following viscosity: 0.18 dl/g.

EXAMPLE 4

Following the general procedure of Example 1, 1080 g. of lactic acid were condensed with 252 g. of glycolic acid in the presence of a total of 25.0 g. of Dowex HCR-W2-H ion exchange polymerization catalyst to give, after removal of the catalyst, 750 g. of a copolymer which was shown by NMR to consist of about 79 percent lactic units and about 21 percent glycolic units. The copolymer exhibited the following viscosity: 0.20 dl/g.

EXAMPLE 5

Following the procedure of Example 1, 432 g. of lactic acid were condensed with 101 g. of glycolic acid in the presence of a total of 5.0 g. of Dowex HCR-W2-H ion exchange polymerization catalyst to provide, after work-up, 300 g. of a copolymer derived from about 77 weight percent of lactic acid and about 23 weight percent of glycolic acid. The copolymer had a viscosity of 0.21 dl/g.

EXAMPLE 6

Following the procedure of Example 1, 432 g. of lactic acid were condensed with 101 g. of glycolic acid in the presence of a total of 2.5 g. of Dowex HCR-W2-H ion exchange polymerization catalyst to provide 300 g. of copolymer comprised of about 76 weight percent lactic acid and about 24 weight percent glycolic acid. The copolymer had the following viscosities:
0.12 after 24 hours at 170° C.
0.20 after 24 hours at 185° C.
0.23 after 40 hours at 185° C.

EXAMPLE 7

The procedure of Example 1 was followed to condense 1080 g. of lactic acid with 120 g. of glycolic acid in the presence of a total of 25.0 g. of Dowex HCR-W2-H ion exchange polymerization catalyst. After workup, there was recovered 750 g. of a copolymer comprised of about 89 weight percent of lactic acid and about 11 weight percent of glycolic acid having the following viscosity: 0.20 dl/g.

EXAMPLE 8

Preparation of Spray Dried Formulation Containing Tylosin

A solution of 50.0 g. of tylosin (free base) in 150 ml. of dichloromethane was added in one portion to a stirred solution of 50.0 g. of the copolymer prepared as described in Example 2 in 200 ml. of dichloromethane. Fresh dichloromethane was added to the mixture until the solution volume was 400 ml. The solution was stirred at room temperature and then spray dried in a conventional spray drier having a pressure tank head pressure of 10 psi and an atomization pressure of 1 psi. The inlet temperature of the spray drier was about 54° to about 57° C., and the spray rate was 8 ml. per minute. The spray-dried product was ground to uniformity and passed through a No. 60 U.S. Standard Mesh Screen. The formulated product so formed can be suspended in a sesame oil carrier for convenient subcutaneous injection into an animal suffering from microbial infection or in need of prophylactic treatment against such infection.

EXAMPLE 9

Preparation of Spray Dried Formulation Containing Apramycin

To a stirred solution of 15.0 g. of copolymer from Example 1 in 40 ml. of dichloromethane was added in one portion 5.0 g. of apramycin free base. The solution was diluted to 80 ml. with additional dichloromethane. The solution then was spray dried at the rate of 10 ml. per minute in a spray drier with inlet temperature from about 48° to about 51° C. and atomization pressure of 1 psi. The spray dried formulation was ground and passed through a No. 60 mesh screen to afford a uniformly sized controlled release formulation of apramycin. The formulation can be suspended in a suitable vehicle and injected subcutaneously into an animal suffering from bacterial pneumonia.

EXAMPLE 10

To a solution of 5.0 g. of copolymer prepared as described in Example 4 (about 80 percent lactic units and about 20 percent glycolic units, inherent viscosity of about 0.18 to about 0.20) in 50 ml. of chloroform was added in one portion 5.0 g. of tylosin as the free base. The solution was stirred for several minutes and then the solvent was removed by evaporation under reduced pressure. The product so formed was extruded into rods of about 5.0 millimeters diameter, such rods resembling an amber glass. The glass rods were ground to uniformity and passed through a screen having mesh of about 60 to about 140. The screened formulation so formed can be suspended in a suitable carrier such as sesame oil or 10 percent aqueous polyvinylpyrrolidone.

EXAMPLE 11

The controlled release tylosin glass-like formulation of Example 10 was evaluated in mice for its ability to uniformly release an effective amount of active agent over a prolonged period of time. The method utilized was similar to that reported by Ose et al. in *J. Vet. Res.*, 29, 1863–1866 (1968). Mice weighing about 20.0 grams were administered, by subcutaneous injection, 25 mg. of the formulation (active ingredient 12.5 mg. per animal) and then challenged with $\log_{10}$ dilutions of a tryptose broth culture of *Erysipelothrix rhusiopathiae* at various time periods. Control groups of non-medicated mice also were challenged at the same rate as the test groups. The $LD_{50}$ of the treated animals and the control animals was calculated at various time intervals. The numerical difference represents $\log_{10}$ protection units attributable to the treatment, thus indicating the degree of protection over a prolonged period. The results of such experiment are presented below.

| Treatment | $\log_{10}$ units of protection | | | | |
| --- | --- | --- | --- | --- | --- |
| | Day 7 | Day 10 | Day 14 | Day 18 | Day 21 |
| Controlled release of tylosin 12.5 mg./animal | 5.5 | 4.8 | 1.3 | 1.0 | 0.2 |

Measurable amounts of tylosin were determined in the urine of the treated animals for 18 days following administration.

EXAMPLE 12

A formulation comprised of 50 percent by weight of Tylosin in a copolymer made up of about 80 percent lactic acid and about 20 percent glycolic acid was extruded into the form of a glass rod. The rod was cut into portions weighing 25 mg., such that the dose of Tylosin was 12.5 mg. per glass rod. The rods so prepared were implanted into mice, and the degree of release of active agent was indicated by measuring $\log_{10}$ units of protection at various intervals following treatment, according to the method described in Example 11. The results are presented in the following table:

| Treatment | $\text{Log}_{10}$ units of Protection | | | | | |
|---|---|---|---|---|---|---|
| | Day 1 | 7 | 11 | 14 | 17 | 21 | 28 |
| Implanted Tylosin 12.5 mg. | >6.0 | >5.3 | 4.2 | 6.0 | 5.7 | 3.3 | 1.2 |

The tests described in Examples 11 and 12 demonstrate that various controlled release tylosin formulations are effective in providing protection from disease by the slow release of antibiotic for periods up to 28 days following administration.

EXAMPLE 13

A formulation of this invention was prepared by mixing a solution of 5 g. of erythromycin in dichloromethane with a dichloromethane solution of 5.0 g. of a copolymer derived from about 79 weight percent lactic acid and about 21 weight percent glycolic acid (viscosity about 0.20). The solution was spray dried by following the general procedure set forth in Example 8. The product thus formed was a dry powder of uniform consistency. The powder was passed through a wire seive of 60 to 140 mesh. The formulation so formed was separated into 25 mg. portions (each containing 12.5 mg. of erythromycin) and suspended in 0.2 ml. of 10% polyvinylpyrrolidone. The formulations thus prepared were injected (12.5 mg/mouse) subcutaneously into mice infected with *Erysipelothrix rhusiopathiae*. A control group of infected mice received one dose of aqueous erythromycin at the rate of 12.5 mg/mouse. The $\text{Log}_{10}$ units of protection against an *Erysipelothrix rhusiopathiae* challenge was determined at various time intervals following dosing. The results are presented below.

| Treatment | $\text{Log}_{10}$ units of protection | | | |
|---|---|---|---|---|
| | day 1 | day 2 | day 3 | day 5 |
| Group treated with controlled release formulation | 4.1 | 3.4 | 1.9 | 0 |
| Group treated with aqueous erythromycin | 1.3 | 0 | 0 | 0 |

The data demonstrates that a single dose of controlled release formulation provides continuous protection for several days, whereas a single dose of conventional active agent affords only minimal protection for a short period of time.

EXAMPLE 14

A formulation comprised of 50 percent by weight of tetracycline and 50 percent by weight of a copolymer derived from about 80 weight percent lactic acid and about 20 weight percent glycolic acid (viscosity about 0.23) was prepared and spray dried according to the method of Example 8. The formulation thus prepared was suspended in a sesame oil vehicle. On day 1, 12.5 mg. of the formulation (6.25 mg/mouse of active ingredient), was administered by subcutaneous injection to a test group of mice. The mice were then challenged with *Pasteurella multocida*. A control group of mice similarily challenged were treated on day 1 with aqueous tetracycline at the rate of 6.25 mg/mouse. As described hereinabove, the $\text{log}_{10}$ units of protection for the two groups were determined at various intervals following treatment. The results are presented in the following table:

| Treatment | $\text{Log}_{10}$ units of Protection | | | |
|---|---|---|---|---|
| | Day 1 | Day 2 | Day 3 | Day 5 |
| Controlled release tetracycline | ≧4.8 | ≧7.6 | >5.0 | ≧4.9 |
| aqueous tetracycline | 3.9 | 3.2 | 0.8 | — |

The controlled release formulation afforded protection against several $\log_{10}$ challenge dilutions at each challenge interval over a prolonged period of time, whereas the aqueous tetracycline failed to afford significant protection beyond the second day.

EXAMPLE 15

The tylosin controlled release formulation prepared according to Example 10 was analyzed in young chickens for its effect on *Mycoplasma gallisepticum*, the causative agent of chronic respiratory disease in poultry. Groups of young chickens were challenged by injection into the thoracic air sac with 0.1 ml. of a broth culture of *Mycoplasma gallisepticum* at 5 or 10 days following a single subcutaneous administration of the tylosin formulation of the invention (25 mg/chicken of formulation, 12.5 mg/chicken of active ingredient). A control group of chickens were infected at the same intervals as the treated group, but the control group received no medication. Various animals from the two groups were sacrificed at various time intervals and analyzed for the presence or absence of air sac lesions. At day 5 following the initial challenge with *Mycoplasma gallisepticum*, twelve animals from each group were analyzed. Of the treated group, none had evidence of air sac lesions. In contrast, nine out of the twelve nonmedicated animals had air sac lesions. At day 10 following the initial infection, only four out of twelve treated animals had air sac lesions, whereas nine out of eleven nonmedicated animals showed significant air sac lesions.

EXAMPLE 16

A controlled release formulation containing 50 percent by weight of the aminoglycoside antibiotic neomycin and 50 percent by weight of a copolymer derived from about 80 weight percent of lactic acid and about 20 weight percent of glycolic acid was prepared by the spray drying process described in Example 8. The formulation was suspended in sesame oil and subcutaneously injected into a group of 1-day old chicks at the rate of 10 mg per chick (active ingredient at the rate of 5 mg per chick). Another group of animals were held as controls and received no antibacterial agent, while still another group of animals received a single injection of aqueous neomycin at the rate of 5 mg per chick. Selected groups of the treated animals were challenged at day 1, day 3 and day 5, respectively, with *Escherichia coli*. The following table shows the number of animals that died out of each of the three groups receiving challenge.

| Treatment | No. died/No. treated (percent deaths) | | |
|---|---|---|---|
| | Challenge at Day 1 | Challenge at Day 3 | Challenge at Day 5 |
| Control group infected, no treatment | 9/20 (45%) | 20/20 (100%) | 20/20 (100%) |

| Treatment | No. died/No. treated (percent deaths) | | |
|---|---|---|---|
| | Challenge at Day 1 | Challenge at Day 3 | Challenge at Day 5 |
| Control group infected, receiving aqueous neomycin | 4/20 (20%) | 19/19 (100%) | 14/14 (100%) |
| Infected group receiving controlled release neomycin | 1/20 (5%) | 1/16 (6.3%) | 3/10 (30%) |

The data demonstrates that a formulation of this invention provides continuous protection over a prolonged period of time, whereas conventional treatment provides only light protection for a relatively short period of time (one day).

EXAMPLE 17

As pointed out hereinabove, a particularly preferred method of treatment according to this invention comprises administering a controlled release formulation provided herein to a new-born animal, such as a pig, thereby protecting the animal from developing a microbial disease during the time that such animal is nursing.

The following experiment was carried out to illustrate the effectiveness of the tylosin controlled release formulation of this invention in protecting pigs from developing mycoplasmal pneumonia during the time they are nursing. Sixteen pigs less than one week of age were inoculated intranasally with a suspension of mycoplasmal pneumonia infected lung tissue. They were placed in one-half of a Horsfal-Bauer isolation unit which had been divided with an open mesh grid into two equal-sized compartments. These pigs were considered seeder pigs and served to provide exposure to treated and nonmedicated control pigs equivalent to the exposure provided to a litter by the sow.

Two weeks later, sixteen neonatal pigs were placed in the unoccupied sides of the isolation units as representative of new-born pigs. Eleven of the new pigs were treated with a 50 percent tylosin-copolymer controlled release formulation (prepared as described in Example 10). The formulation was suspended in sesame oil containing 1.5 percent by weight of beeswax and 1.5 percent by weight of aluminum monostearate. The animals received an intramuscular injection on day zero of sufficient quantity that each pig received 250 mg. of tylosin (i.e. 500 mg of the controlled release formulation). On the tenth day of the experiment, the treated pigs received a second injection of such size that each pig received 375 mg. of tylosin, and again on the twentieth day the treated animals were administered 500 mg of active ingredient (1000 mg of the formulation). Five pigs were not medicated and were included as controls to demonstrate that transmission of mycoplasmal pneumonia from the seeders would occur. All pigs were killed on the 34th day following placement of the second group of pigs in the units. Lungs were isolated and examined for gross lesions, (an indication of infection), and cultures from lung tissue were made for *Mycoplasma hyopneumoniae*. As shown in the accompanying summary table, out of nine tylosin controlled release treated pigs, none were infected, as determined by gross lung lesions or reisolation of *M. hyopneumoniae* from the lung. In contrast, mycoplasmal pneumonia was transmitted to three of the five nonmedicated controls. The two deaths that occurred in the treated group and the one seeder pig that died during the study were due to causes other than mycoplasmal pneumonia.

Tylosin Controlled Release Treatment of *Mycoplasma hyopneumoniae* Exposed Pigs

| Pig No. | Tylosin Treatment | Gross Lung Lesions | | Isolation of *M. hyopneumoniae* from Lung tissue | |
|---|---|---|---|---|---|
| | | Treated | Seeder | Treated | Seeder |
| 1 | Tylosin C.R., IM | Normal | 10%* | — | + |
| 2 | 0 day - 500 mg/pig | Normal | 25% | — | + |
| 3 | 10 day - 750 mg/pig | Normal | 15% | — | + |
| 4 | 20 day - 1000 mg/pig | Normal | 1% | — | + |
| 5 | | Normal | Died | — | 0 |
| 6 | | Normal | 20% | — | + |
| 7 | | Died | 4% | 0 | + |
| 8 | | Normal | 10% | — | — |
| 9 | | Normal | 3% | — | + |
| 10 | | Normal | 2% | — | + |
| 11 | | Died | 2% | 0 | + |
| 1 | Nonmedicated controls | Normal | 5% | — | + |
| 2 | | 2% | 5% | + | + |
| 3 | | 7%. | 5% | + | + |
| 4 | | Normal | Trace | — | + |
| 5 | | 10% | 10% | + | + |

*percentage of lungs with gross pneumonic lesions

The results of the study demonstrate that new-born animals exposed to mycoplasmal pneumonia can be effectively protected against contacting such disease by treatment according to this invention. A single parenteral administration of a controlled release formulation of this invention provides protection to such animals for periods of about seven to about twelve days. Longer periods of protection, for instance from about fourteen to about twenty-one days, can be achieved by administering the formulations by implantation and the like.

EXAMPLE 18

A formulation comprised of fifty percent doxycycline and fifty percent of a copolymer derived from about 80 weight percent lactic acid and about 20 weight percent glycolic acid was prepared by the method of Example 8. The formulation so prepared was administered by a single subcutaneous injection (in sesame oil) to a group of mice at the rate of 25 mg/mouse (effective dose of doxycycline therefore was 12.5 mg/mouse). Another group of mice received a single dose of aqueous doxycycline at the rate of 12.5 mg/mouse. Following medication, all of the animals were challenged at various time intervals with *Pasteurella multocida*. The following table presents the $\log_{10}$ protection units at various time intervals following treatment and subsequent challenge.

| Treatment | $\log_{10}$ protection post treatment | | |
|---|---|---|---|
| | Day 0 | Day 3 | Day 5 |
| aqueous doxycycline | 3.3 | 0 | 1.2 |
| controlled release doxycycline | ≧5.8 | ≧5.3 | ≧6.7 |

The results demonstrate that controlled release doxycycline of this invention provides protection against ≧5.3 $\log_{10}$ *Pasteurella multocida* challenge units at each challenge period. In contrast, aqueous doxycycline provides little protection beyond the initial treatment and challenge.

EXAMPLE 19

As already pointed out, a preferred formulation of this invention comprises a cephalosporin antibacterial agent intimately dispersed throughout a copolymer as hereinabove defined. Especially preferred cephalosporin antibiotics to be utilized include the 7-α-methoxyimino-α-(2-aminothiazol-4-yl)acetamido-3-substituted-3-cephem-4-carboxylic acids or salts, wherein the 3-substituent is, inter alia, methyl, 5-methyl-(1,3,4-thiadiazol-2-yl) thiomethyl, (1-methyl-5,6-dioxo-1,3,4-triazin-2-yl)thiomethyl, (1-carboxymethyl-1,2,3,4-tetrazol-5-yl)thiomethyl and (1,2,3,4-tetrazole-5-yl)-thiomethyl.

A typical cephalosporin commonly utilized in the formulations of the invention is 3-methyl-7-α-methoxyimino-α-(2-aminothiazol-4-yl)acetamido-3-cephem-4-carboxylic acid. Such compound was dissolved in an organic solvent such as dichloromethane at the rate of about 100 mg in 100 ml. of solvent. About 100 mg of a copolymer derived from about 80 weight percent lactic acid and about 20 weight percent glycolic acid, with a viscosity of about 0.20, was added to the solution. The solution was then spray dried by the method of Example 8 to give a uniform mixture of active agent and copolymer. The formulation thus formed was suspended in 20 ml. of sesame oil.

In a test designed to demonstrate the controlled release of active ingredient from the above formulation, one group of mice were given a single subcutaneous injection of 12.5 mg. of 3-methyl-7-α-methoxyimino-α-(2-aminothiazol-4-yl)acetamido-3-cephem-4-carboxylic acid (cephalosporin acid). Another group of mice were given a single subcutaneous injection of 25 mg of the controlled release formulation (controlled release cephalosporin acid), so that the dose of active ingredient was 12.5 mg. per mouse. The animals were then challenged at various time intervals with *Pasteurella multocida*. The following table shows the results of the treatments in units of $\log_{10}$ protection at various days post-treatment for the two treated groups.

| Treatment | $\log_{10}$ protection at various days post-treatment | | | |
|---|---|---|---|---|
| | Day 0 | Day 1 | Day 3 | Day 5 |
| cephalosporin acid | ≧5.2 | 0.7 | 0 | 0.4 |
| controlled release cephalosporin acid | ≧5.2 | ≧4.4 | ≧4.5 | ≧4.7 |

The data makes clear the fact that a single treatment with a controlled release formulation of this invention protects the host animal for several days, whereas a corresponding single dose of the active ingredient alone affords protection for no more than one day.

We claim:

1. A controlled release formulation capable of delivering an effective dose of active ingredient over a prolonged period of time and biodegradable into readily metabolized substances and normal active ingredient metabolic products comprising about 5 to about 85 percent by weight of active ingredient intimately dispersed throughout a copolymer derived from about 60 to about 95 weight percent lactic acid and about 40 to about 5 weight percent glycolic acid, said copolymer having an inherent viscosity of about 0.08 to about 0.30 when measured in chloroform, a molecular weight of about 6000 to about 35000, and said copolymer being substantially free of polymerization catalyst.

2. The formulation of claim 1 wherein the active ingredient is an antimicrobial agent and the formulation is useful in the prophylactic and therapeutic treatment of diseases caused by microorganisms.

3. The formulation of claim 2 wherein the copolymer utilized is derived from about 60 to about 90 percent lactic acid and about 40 to about 10 percent glycolic acid, said copolymer having a viscosity of about 0.10 to about 0.25 and a molecular weight of about 15,000 to about 30,000.

4. The formulation of claim 3 wherein the active ingredient is an antimicrobial agent selected from the group consisting of the penicillins, cephalosporins, tetracyclines, sulfa drugs, macrolide antibiotics, and aminoglycosides.

5. The formulation of claim 3 wherein the active ingredient is an antibacterial agent selected from chlortetracycline, tetracycline, oxytetracycline, doxycycline, ampicillin, benzylpenicillin, penicillin V, cephalosporins, cloxicillin, streptomycin, lincomycin, novobiocin, neomycin, spiramycin, erythromycin, colistin, nalidixic acid, salinomycin, nigericin, kanamycin, kitsamycin, gentamycin, tobramycin, apramycin, furaltadone, vancomycin, thiostrepton, ristocetin, soimycin, tylosin or sulfonamides.

6. The formulation of claim 5 wherein the copolymer matrix is derived from about 70 to about 80 percent lactic acid and about 30 to about 20 percent glycolic acid, having an inherent viscosity of about 0.13 to about 0.23.

7. The formulation of claim 6 wherein the active ingredient is selected from the group consisting of tetracycline, oxytetracycline, doxycycline, lincomycin, spiramycin, neomycin, erythromycin, tylosin, and 3-methyl-7-α-methoxyimino-α-(2-aminothiazol-4-yl)acetamido-3-cephem-4-carboxylic acid.

8. The formulation of claim 7 comprising about 20 to about 75 percent by weight of active ingredient uniformly admixed with a copolymer matrix derived from about 70 to about 80 weight percent lactic acid and about 30 to about 20 percent glycolic acid, said copolymer having a viscosity of about 0.13 to about 0.23.

9. The formulation of claim 8 wherein the active ingredient is present in about 30 to about 60 percent by weight.

10. The formulation of claim 9 wherein the active ingredient is doxycycline.

11. The formulation of claim 9 wherein the active ingredient is oxytetracycline.

12. The formulation of claim 9 wherein the active ingredient is 3-methyl-7-α-methoxyimino-α-(2-aminothiazol-4-yl)acetamido-3-cephem-4-carboxylic acid.

13. The formulation of claim 9 wherein the active ingredient is lincomycin.

14. The formulation of claim 9 wherein the active ingredient is spiramycin.

15. The formulation of claim 9 wherein the active ingredient is erythromycin.

16. The formulation of claim 9 wherein the active ingredient is neomycin.

17. The formulation of claim 9 wherein the active ingredient is tylosin.

18. The formulation of claim 17, said formulation comprising about 30 to about 60 percent by weight of tylosin admixed with from about 70 to about 40 percent by weight of a copolymer derived from about 70 to about 80 percent by weight of lactic acid and about 30 to about 20 percent by weight of glycolic acid.

19. The formulation of claim 17, said formulation comprised of about 40 percent tylosin admixed with a copolymer derived from about 80 percent lactic acid and about 20 percent glycolic acid, said copolymer having a viscosity of about 0.18 to about 0.23.

20. The formulation of claim 17, said formulation comprised of about 50 percent by weight of tylosin admixed with a copolymer derived from about 80 percent lactic acid and about 20 percent glycolic acid having a viscosity of about 0.18 to about 0.23.

21. The formulation of claim 17, said formulation comprised of about 55 percent by weight of tylosin admixed with a copolymer derived from about 80 percent lactic acid and about 20 percent glycolic acid having a viscosity of about 0.18 to about 0.23.

22. The formulation of claim 17 in the form of extruded glass-like rods having a diameter of about 2 to about 7 mm.

23. The formulation of claim 17 in the form of extruded glass-like rods being ground to uniformity and passed through a sieve having mesh of about 60 to about 140.

24. A method of treating microbial infections in animals comprising administering an effective amount of a formulation of claim 1.

25. A method of treating microbial infections in animals comprising administering an effective amount of the formulation of claim 5.

26. A method of treating animals suffering from a microbial infection and in need of treatment comprising administering an effective amount of the formulation of claim 7.

27. A method of treating animals suffering from a microbial infection and in need of treatment comprising administering an effective amount of the formulation of claim 9.

28. A method of treating animals suffering from a microbial infection and in need of treatment comprising administering an effective amount of the formulation of claim 18.

29. The method of claim 28 wherein the microbial infection is pneumonia.

30. The method of claim 29 wherein the host is a young calf.

31. A method of treating a young calf suffering from pneumonia and in need of treatment comprising administering to said calf an effective amount of the formulation of claim 18.

32. The method of claim 31 wherein the formulation is in the form of an extruded glass-like rod and administered by subcutaneous implantation.

33. The method of claim 31 wherein the formulation is in the form of a uniformly ground extruded glass-like rod suspended in a suitable pharmaceutical vehicle.

34. The method of claim 33 wherein the formulation is administered by subcutaneous injection.

35. A method for the prophylactic treatment of microbial infections in animals comprising the administration of an effective amount of the formulation of claim 1.

36. A method for the prophylactic treatment of microbial infections in animals comprising the administration of an effective amount of the formulation of claim 7.

37. A method for the prophylactic treatment of microbial infections in animals comprising the administration of an effective amount of the formulation of claim 18.

38. The method of treatment of claim 37 wherein the host animal is a ruminant.

39. The method of claim 38 wherein the animal is a young calf.

40. The method of claim 39 wherein the microbial infection being treated is pneumonia.

41. The method of claim 37 wherein the host animal is swine.

42. The method of claim 41 wherein the animal treated is a young pig.

43. The method of claim 42 wherein the animal treated is a new born pig.

44. The method of claim 41 wherein the disease guarded against is pneumonia.

45. The method of claim 43 wherein the disease guarded against is mycoplasmal pneumonia.

46. The method of claim 37 wherein the host animal is a chicken.

47. The method of claim 46 wherein the disease guarded against is pneumonia.

48. The method of claim 37 wherein the disease guarded against is chronic respiratory disease.

* * * * *